(12) United States Patent
Zheng et al.

(10) Patent No.: US 11,832,634 B2
(45) Date of Patent: Dec. 5, 2023

(54) PIGLET FEED BASED ON BACTERIAL ENZYME SYNERGISTIC FERMENTATION PROCESS AND PREPARATION METHOD THEREOF

(71) Applicant: Sichuan Agricultural University, Chengdu (CN)

(72) Inventors: Ping Zheng, Chengdu (CN); Daiwen Chen, Chengdu (CN); Bing Yu, Chengdu (CN); Jun He, Chengdu (CN); Jie Yu, Chengdu (CN); Zou Xia, Chengdu (CN)

(73) Assignee: SICHUAN AGRICULTURAL UNIVERSITY, Chengdu (CN)

( * ) Notice: Subject to any disclaimer, the term of this patent is extended or adjusted under 35 U.S.C. 154(b) by 144 days.

(21) Appl. No.: 17/316,728

(22) Filed: May 11, 2021

(65) Prior Publication Data
US 2022/0361524 A1  Nov. 17, 2022

(51) Int. Cl.
| | |
|---|---|
| A23K 10/14 | (2016.01) |
| A23K 20/147 | (2016.01) |
| A23K 10/22 | (2016.01) |
| A23K 20/22 | (2016.01) |
| A23K 20/26 | (2016.01) |
| A23K 20/174 | (2016.01) |
| A23K 10/30 | (2016.01) |
| A23K 20/163 | (2016.01) |
| A23K 20/158 | (2016.01) |
| A23K 20/24 | (2016.01) |
| A23K 20/20 | (2016.01) |
| A23K 20/105 | (2016.05) |
| A23K 50/30 | (2016.01) |
| A23K 50/60 | (2016.01) |
| A61K 35/747 | (2015.01) |
| A61K 35/744 | (2015.01) |
| A61K 36/062 | (2006.01) |
| A61K 9/00 | (2006.01) |
| A61K 33/34 | (2006.01) |
| A61K 33/26 | (2006.01) |
| A61K 33/32 | (2006.01) |
| A61K 33/06 | (2006.01) |
| A61K 33/04 | (2006.01) |
| A61K 31/198 | (2006.01) |
| A61K 31/405 | (2006.01) |
| A61K 31/07 | (2006.01) |
| A61K 31/593 | (2006.01) |
| A61K 31/355 | (2006.01) |
| A61K 31/122 | (2006.01) |
| A61K 31/51 | (2006.01) |
| A61K 31/525 | (2006.01) |

(Continued)

(52) U.S. Cl.
CPC .............. *A23K 10/14* (2016.05); *A23K 10/16* (2016.05); *A23K 10/22* (2016.05); *A23K 10/30* (2016.05); *A23K 20/105* (2016.05); *A23K 20/147* (2016.05); *A23K 20/158* (2016.05); *A23K 20/163* (2016.05); *A23K 20/174* (2016.05); *A23K 20/22* (2016.05); *A23K 20/24* (2016.05); *A23K 20/26* (2016.05); *A23K 20/30* (2016.05); *A23K 50/30* (2016.05); *A23K 50/60* (2016.05); *A61K 9/0056* (2013.01); *A61K 31/07* (2013.01); *A61K 31/122* (2013.01); *A61K 31/197* (2013.01); *A61K 31/198* (2013.01); *A61K 31/355* (2013.01); *A61K 31/375* (2013.01); *A61K 31/405* (2013.01); *A61K 31/4188* (2013.01); *A61K 31/4415* (2013.01); *A61K 31/455* (2013.01); *A61K 31/51* (2013.01); *A61K 31/519* (2013.01); *A61K 31/525* (2013.01); *A61K 31/593* (2013.01); *A61K 31/714* (2013.01); *A61K 33/04* (2013.01); *A61K 33/06* (2013.01); *A61K 33/26* (2013.01); *A61K 33/32* (2013.01); *A61K 33/34* (2013.01); *A61K 35/744* (2013.01); *A61K 35/747* (2013.01); *A61K 36/062* (2013.01); *A23V 2400/169* (2023.08); *A23V 2400/427* (2023.08)

(58) Field of Classification Search
CPC ........ A23K 10/14; A23K 10/16; A23K 10/22; A23K 10/30; A23K 20/105; A23K 20/147; A23K 20/158; A23K 20/163; A23K 20/174; A23K 20/22; A23K 20/24; A23K 20/26; A23K 20/30; A23K 50/30; A23K 50/60; A23K 10/12; A23K 10/18; A23K 20/142; A23K 20/189; A23K 20/28; A61K 9/0056; A61K 31/07; A61K 31/122; A61K 31/197; A61K 31/19; A61K 31/198; A61K 31/355; A61K 31/375; A61K 31/405; A61K 31/4188; A61K 31/4415; A61K 31/455; A61K 31/51; A61K 31/519; A61K 31/525; A61K 31/593; A61K 31/714; A61K 33/04; A61K 33/06; A61K 33/26; A61K 33/32; A61K 33/34; A61K 35/744; A61K 35/747; A61K 36/062; A61K 35/00; A23Y 2220/67; A23Y 2280/55; A23Y 2220/06; Y02P 60/87
See application file for complete search history.

*Primary Examiner* — Kade Ariani

(57) ABSTRACT

Disclosed is a piglet feed based on bacteria enzyme synergistic fermentation process. The piglet feed is composed of basic components and bacteria enzyme synergistic fermentation feed. Basic components include soybean protein concentrate, whey powder, fish meal, sodium chloride, choline chloride, stone powder, calcium hydrogen phosphate, composite vitamins, composite trace elements, and composite amino acids. The bacterial enzyme synergistic fermentation feed includes a fermentation substrate, an enzyme preparation, and a bacterial strain. The bacterial enzyme synergistic fermentation feed can not only improve the production performance of piglets, but also improve the utilization rate (Continued)

of feed nutrients, especially the utilization rate of feed phosphorus, thereby reducing the excretion of phosphorus in feces.

9 Claims, No Drawings

(51) Int. Cl.
*A61K 31/4415* (2006.01)
*A61K 31/714* (2006.01)
*A61K 31/197* (2006.01)
*A61K 31/4188* (2006.01)
*A61K 31/519* (2006.01)
*A61K 31/455* (2006.01)
*A61K 31/375* (2006.01)
*A23K 10/16* (2016.01)

PIGLET FEED BASED ON BACTERIAL ENZYME SYNERGISTIC FERMENTATION PROCESS AND PREPARATION METHOD THEREOF

TECHNICAL FIELD

This disclosure relates to the field of animal breeding and feed production, and in particularly to a piglet feed based on a bacterial enzyme synergistic fermentation process and a preparation method thereof.

BACKGROUND

Phosphorus is one of the essential mineral elements for animals and plays an important role in the growth of animals. As a non-renewable resource, phosphorus is the third most expensive feed material in the feed industry after protein and energy. Phosphorus is an important part of animal bones and teeth. It is also an important part of genetic material and most enzymes. Its biological functions are the most among mineral elements, which include: (1) participating in the formation of bones and teeth; (2) constituting ATP and creatine phosphate, participating in the body's energy metabolism; (3) promoting the absorption of lipids and fat-soluble vitamins in the form of phospholipids, and ensuring the integrity of biological membranes; (4) being an important part of genetic material such as DNA and RNA and also participating in the formation of most enzymes; and (5) forming the $Na_2HPO_4/Na_2H_2PO_4$ buffer pair to regulate the acid-base balance.

However, the current utilization efficiency of phosphorus in animal production is generally low, and a large amount of unused phosphorus is excreted with feces and urine, which makes the environment continuously enriched in phosphorus, causing environmental pollution such as eutrophication of water bodies. Phosphorus in plant feeds exists in two forms: phytate phosphorus and non-phytate phosphorus. The common one is phytate phosphorus which has low availability. The phytate phosphorus also interacts with protease inhibitors, plant lectins, saponin, tannins and other anti-nutrient substances, which further affects the utilization of mineral elements such as calcium, zinc, magnesium, copper, manganese, cobalt, iron, etc. At the same time, the phosphoric acid group on phytic acid may interact with the cationic groups on the protein, amino acids, starch, lipid in the feed, and makes its solubility reduced, which will affect the digestibility of these nutrients by animals, especially for pigs. The phytate phosphorus also interacts with amylase, pepsin, trypsin and acid phosphatase to reduces the activity of these enzymes and reduces the nutrient utilization of the entire diet.

Insufficient phosphorus supply in diets can lead to weakened metabolic activity, decreased appetite, slower growth rate, decreased productivity, abnormal bone development, etc., and clinical symptoms such as rickets and osteomalacia. In order to meet the growth needs of pigs and achieve the best production, inorganic phosphorus sources are usually added to the diet, especially phosphate phosphorus, which usually accounts for ⅓ of the total phosphorus in the feed. However, due to the low digestibility and utilization of phosphorus, a large amount of undigested and absorbed phosphorus is excreted with feces, and enters rivers and lakes through surface runoff and infiltration, resulting in eutrophication of water bodies, leading to the growth and reproduction of algae and other plankton microorganisms. The amount of dissolved oxygen in the water body decreases and the water quality deteriorates, causing a large number of deaths of fish and other aquatic animals. Therefore, a large amount of phosphorus discharged into the environment will have a great impact on the ecological balance.

In order to improve the utilization of feed phosphorus, the main method currently used is to add phytase to the feed to hydrolyze the phytic acid in the plant feed. The characteristic of this method is that the phosphorus in plant feed mainly exists in the form of phytate phosphorus. Because piglets lack phytase that decomposes phytate phosphorus and microorganisms that can produce phytase, the utilization rate of feed phytate phosphorus is low. Accordingly, by adding phytase to effectively release the phosphorus in the plant feed so that the piglet can absorb and utilize it, thereby improving the utilization rate of phosphorus in feed materials. However, this method can only partially improve the utilization of feed phosphorus. The rate of improvement is limited. Therefore, the existing method has defects and needs further improvement and perfection.

SUMMARY OF THIS DISCLOSURE

The object of the present disclosure is to construct a bacterial enzyme synergistic fermentation process and its product according to the features of enzymes, substrates and microorganisms, combine with the principle of functional complementarity and superposition. The bacterial enzyme synergistic fermentation feed can not only improve the production performance of piglets, but also increase the utilization rate of feed nutrients, especially the utilization rate of feed phosphorus, so as to reduce the excretion of phosphorus in feces.

This disclosure is specified as follows. All percentages expressed on a weight basis.

A piglet feed based on bacterial enzyme synergistic fermentation process is provided. The piglet feed consists of 10-20% basic components and 80-90% bacterial enzyme synergistic fermentation feed.

The basic component comprises 26.67% soy protein concentrate, 26.67% whey powder, 26.67% fish meal, 2.67% sodium chloride, 0.8% choline chloride, 6% stone powder, 3.46% hydrogen phosphate calcium, 0.33% compound vitamins, 1.33% compound trace elements, and 5.4% compound amino acids. All percentages expressed on a weight basis.

The bacterial enzyme synergistic fermentation feed comprises a fermentation substrate, an enzyme preparation, and a bacterial strain.

A total of 100% of the fermentation substrate comprises 36% corn, 36% expanded corn, 12% soybean meal, 12% expanded soybean, 2% sucrose, and 2% soybean oil. All percentages expressed on a weight basis.

Furthermore, in the bacterial enzyme synergistic fermentation feed, the total concentration of the bacterial strain is $1\text{-}2\times10^8$ (CFU/mL). Based on the fermentation substrate, the enzyme preparation is added by 0.1-0.2%.

Furthermore, the enzyme preparation is composed of 0.03-0.06% protease, 0.03-0.06% amylase, 0.02-0.04% lipase, and 0.02-0.04% cellulase.

Furthermore, the bacterial strain is composed of *Lactobacillus plantarum* (CGMCC1.12934), *Pediococcus pentosaceus* (CGMCC1.12961), and *Aspergillus niger* (CGMCC3.4304). Preferably, the bacterial strain consists of 1-2 mL of *Lactobacillus plantarum* (CGMCC1.12934), 1-2 mL of *Pediococcus pentosaceus* (CGMCC1.12961), and 1-2 mL of *Aspergillus niger* (CGMCC3.4304).

Furthermore, the multivitamin comprises vitamin A, vitamin D3, vitamin E, vitamin K3, vitamin B1, vitamin B2, vitamin B6, vitamin B12, calcium pantothenate, folic acid, biotin, niacin, and vitamin C.

Furthermore, the composite trace element comprises copper sulfate, ferrous sulfate, manganese sulfate, calcium iodate, and ultrafine sodium selenite.

Further, the composite amino acid comprises lysine, methionine, threonine, and tryptophan.

The preparation method of the piglet feed comprises the following steps:
(1) providing *Lactobacillus plantarum* (CGMCC1.12934), *Pediococcus pentosaceus* (CGMCC1.12961), *Aspergillus niger* (CGMCC3.4304);
(2) providing protease (>50 000 U/g), amylase (>7 000 U/g), lipase (>8 000 U/g), cellulase (>10 000 U/g) and mixing them well;
(3) mixing the fermentation substrate uniformly in proportions, adding water according to the ratio of 1:0.5, adding the enzyme preparation and the bacterial strain in sequence during a stirring process, and fermenting at 28-30° C. for 12 h; and
(4) mixing the basic component uniformly in proportions, adding the bacterial enzyme synergistic fermentation feed prepared in step (3), and mixing them uniformly.

Some of the advantages of the present disclosure is as follows.

According to the characteristics of enzymes, substrates and microorganisms, the present disclosure provides three microorganisms and four enzyme preparations, and for the first time studies the effect of their synergistic fermentation on the phosphorus utilization of piglet feed. The present disclosure combines biochemical analysis methods through piglet feeding test and digestion test to investigate the effects of bacterial enzyme synergistic fermentation feed on piglet production performance and the apparent digestibility of feed phosphorus. Then a feed based on the bacterial enzyme synergistic fermentation process that can increase the phosphorus utilization rate of the piglet's diet by 50% was prepared.

The product of the present disclosure can significantly improve the growth performance of piglets, increase the digestibility of feed nutrients, especially the utilization rate of phosphorus in the feed.

DETAILED DESCRIPTION OF THE DISCLOSURE

A piglet feed based on bacterial enzyme synergistic fermentation process is provided. The piglet feed is consisted of 15% basic components and 85% bacterial enzyme synergistic fermentation feed. All percentages expressed on a weight basis.

A total of 100% of the basic component comprises 26.67% soy protein concentrate, 26.67% whey powder, 26.67% fish meal, 2.67% sodium chloride, 0.8% choline chloride, 6% stone powder, 3.46% hydrogen phosphate calcium, 0.33% compound vitamins, 1.33% compound trace elements, 5.4% compound amino acids. All percentages expressed on a weight basis.

The bacterial enzyme synergistic fermentation feed comprises a fermentation substrate, an enzyme preparation, and a bacterial strain.

A total of 100% of the fermentation substrate comprises 36% corn, 36% expanded corn, 12% soybean meal, 12% expanded soybean, 2% sucrose, and 2% soybean oil. All percentages expressed on a weight basis.

In the bacterial enzyme synergistic fermentation feed, the total concentration of the bacterial strain is $2 \times 10^8$ (CFU/mL). Based on the fermentation substrate, the enzyme preparation is added by 0.2%. The bacterial strain is composed of *Lactobacillus plantarum* (CGMCC1.12934), *Pediococcus pentosaceus* (CGMCC1.12961), and *Aspergillus niger* (CGMCC3.4304). Preferably, the bacterial strain consists of 1-2 mL of *Lactobacillus plantarum* (CGMCC1.12934), 1-2 mL of *Pediococcus pentosaceus* (CGMCC1.12961), and 1-2 mL of *Aspergillus niger* (CGMCC3.4304). The enzyme preparation is composed of 0.06% protease, 0.05% amylase, 0.04% lipase, and 0.02% cellulase.

The multivitamin comprises vitamin A, vitamin D3, vitamin E, vitamin K3, vitamin B1, vitamin B2, vitamin B6, vitamin B12, calcium pantothenate, folic acid, biotin, niacin, and vitamin C. There is no specific amount of each component, and generally meet the needs of animals. The following trace elements and compound amino acids are also the same.

The composite trace element comprises copper sulfate, ferrous sulfate, manganese sulfate, calcium iodate, and ultrafine sodium selenite. The composite amino acid comprises lysine, methionine, threonine, and tryptophan.

The preparation method of the piglet feed comprises the following steps:
(1) providing *Lactobacillus plantarum* (CGMCC1.12934), *Pediococcus pentosaceus* (CGMCC1.12961), *Aspergillus niger* (CGMCC3.4304);
(2) providing protease (>50 000 U/g), amylase (>7 000 U/g), lipase (>8 000 U/g), cellulase (>10 000 U/g) and mixing them well;
(3) mixing the fermentation substrate uniformly in proportions, adding water according to the ratio of 1:0.5, adding the enzyme preparation and the bacterial strain in sequence during a stirring process, and fermenting at 28-30° C. for 12 h; and
(4) mixing the basic component uniformly in proportions, adding the bacterial enzyme synergistic fermentation feed prepared in step (3), and mixing them uniformly.

The present disclosure has carried out a systematic study on the feed prepared in the examples. The 21-day-old weaned piglet was used as a test animal, and the piglet was fed an unfermented and fermented diet composed of the same raw material to investigate the growth performance, nutrient digestibility and utilization rate of the jejunal digestive enzyme activity.

Example 1

The 21-day-old weaned piglets were used as experimental animals. The method was divided into 2 groups using a randomized block design method, each with 8 replicates and 3 piglets in each replicate. The control group was fed unfermented piglet feed and the test group was fed fermented feed. The test period is 49 days. The average daily feed intake, daily gain, and diarrhea index of piglets are investigated. The results are shown in Table 1. The results showed that compared with the control group, the test group significantly increased the piglet body weight and average daily gain, and significantly reduced the piglet's diarrhea.

TABLE 1

Effect on the Production Performance and Diarrhea Rate of Weaned Piglets

| Item | Control | Test | SEM | Value P |
| --- | --- | --- | --- | --- |
| Initial Weight (kg) | 7.16 | 7.16 | 0.30 | 1.00 |
| Fina Weight (kg) | 25.64 | 28.63 | 0.50 | 0.05 |
| Average Daily Gain (g) | 376 | 437 | 10 | 0.03 |
| Average Daily Feed Intake (g) | 650 | 705 | 14 | 0.22 |
| Feed Conversion Ratio | 1.73 | 1.62 | 0.03 | 0.27 |
| Diarrhea Index | 0.12 | 0.04 | 0.02 | 0.03 |

Example 2

The 21-day-old weaned piglets were used as experimental animals. The method was divided into 2 groups using a randomized block design method, each with 8 replicates and 3 piglets in each replicate. The control group was fed unfermented piglet feed, and the test group was fed fermented feed. The test period is 49 days. The nutrient digestibility of piglets is investigated. The results are shown in Table 2. The results showed that the test group significantly improved the apparent digestibility of dietary dry matter, crude protein, crude fat and phosphorus, and the utilization of phosphorus increased by 52%.

TABLE 2

Effect on the Apparent Digestibility of Nutrients in Weaned Piglets (%)

| Item | Control | Test | SEM | Value P |
| --- | --- | --- | --- | --- |
| Dry Material (DM) | 77 | 84 | 1 | <0.01 |
| Crude Protein (CP) | 67 | 76 | 1 | <0.01 |
| Ether Extract (EE) | 53 | 67 | 2 | <0.01 |
| Ash | 44 | 57 | 2 | <0.01 |
| Total Phosphorus (TP) | 25 | 38 | 2 | 0.03 |

Example 3

The 21-day-old weaned piglets were used as experimental animals, and they were divided into 2 groups using a random block design method, each with 8 replicates, and each replicate with 3 piglets. The control group was fed unfermented piglet feed, and the test group was fed fermented feed. The test period was 49 days. The digestive enzyme activity of the piglet's jejunum is investigated. The results are shown in Table 3.

TABLE 3

Digestive Enzyme Activity

| Item | Control | Test | SEM | Value P |
| --- | --- | --- | --- | --- |
| Sucrase (U/mg prot) | 110 | 168 | 8 | 0.03 |
| Maltase (U/mg prot) | 117 | 115 | 9 | 0.77 |
| Amylase (U/mg prot) | 1.26 | 1.62 | 0.05 | <0.01 |

The results showed that the test group significantly improved the activities of sucrase and amylase in the jejunum mucosa of piglets by 53% and 29%, respectively.

What is claimed is:

1. A piglet feed, wherein the piglet feed consists of 10-20% by weight of a basic component and 80-90% by weight of a bacterial enzyme synergistic fermentation feed;

a total of 100% by weight of the basic component is 26.67% by weight of a soy protein concentrate, 26.67% by weight of a whey powder, 26.67% by weight of a fish meal, 2.67% by weight of a sodium chloride, 0.8% by a weight of a choline chloride, 6% by weight of a stone powder, 3.46% by weight of a hydrogen phosphate calcium, 0.33% by weight of compound vitamins, 1.33% by weight of compound trace elements, and 5.4% by weight of compound amino acids;

the bacterial enzyme synergistic fermentation feed is a fermentation substrate, that is fermented in the presence of a mixture of enzymes and bacterial strains; and a total of 100% by weight of the fermentation substrate comprises 36% by weight of a corn, 36% by weight of a corn, 12% by weight of a soybean meal, 12% by weight of a soybean, 2% by weight of a sucrose, and 2% by weight of a soybean oil.

2. The piglet feed according to claim 1, wherein in the bacterial enzyme synergistic fermentation feed, the total concentration of the bacterial strain is $1-2 \times 10^8$ (CFU/mL).

3. The piglet feed according to claim 1, wherein the enzymes are 0.03-0.06% by weight of a protease, 0.03-0.06% by weight of an amylase, 0.02-0.04% by weight of a lipase, and 0.02-0.04% by weight of a cellulase.

4. The piglet feed according to claim 1, wherein the bacterial strains are *Lactobacillus plantarum*, *Pediococcus pentosaceus*, and *Aspergillus niger*, and each of the bacterial strains.

5. The piglet feed according to claim 1, wherein the bacterial strains are 1-2mL of *Lactobacillus plantarum*, 1-2mL of *Pediococcus pentosaceus*, and 1-2mL of *Aspergillus niger*.

6. The piglet feed according to claim 1, wherein the compound vitamins are vitamin A, vitamin D3, vitamin E, vitamin K3, vitamin B1, vitamin B2, vitamin B6, vitamin B12, calcium pantothenate, folic acid, biotin, niacin, and vitamin C.

7. The piglet feed according to claim 1, wherein the compound trace elements are copper sulfate, ferrous sulfate, manganese sulfate, calcium iodate, and ultrafine sodium selenite.

8. The piglet feed according to claim 1, wherein the compound amino acids are lysine, methionine, threonine, and tryptophan.

9. A method for preparing a piglet feed, wherein the piglet feed is consisted of 10-20% by weight of a basic component and 80-90% by weight of a bacterial enzyme synergistic fermentation feed;

a total of 100% by weight of the basic component is 26.67% by weight of a soy protein concentrate, 26.67% by weight of a whey powder, 26.67% by weight of a fish meal, 2.67% by weight of a sodium chloride, 0.8% by a weight of choline chloride, 6% by weight of a stone powder, 3.46% by weight of a hydrogen phosphate calcium, 0.33% by weight of compound vitamins, 1.33% by weight of compound trace elements, and 5.4% by weight of compound amino acids;

the bacterial enzyme synergistic fermentation feed is a fermentation substrate that is fermented in the presence of enzymes and mixture of bacterial strains; and a total of 100% by weight of the fermentation substrate comprises 36% by weight of a corn, 36% by weight of a corn, 12% by weight of a soybean meal, 12% by weight of a soybean, 2% by weight of a sucrose, and 2% by weight of a soybean oil.

the method for preparing the piglet feed comprises the following steps:

step (1), providing bacterial strains *Lactobacillus plantarum, Pediococcus pentosaceus*, and *Aspergillus niger*;

step (2), providing a mixture of protease (>50 000 U/g), an amylase (>7 000 U/g), a lipase (>8 000 U/g), a cellulase (>10 000 U/g);

step (3), mixing the fermentation substrate uniformly in water in a the ratio of 1:0.5, adding the enzyme mixture and the bacterial strains in sequence during a stirring process, and fermenting at 28-30° C. for 12 h to obtain a bacterial enzyme synergistic fermentation feed; and step (4), mixing the basic component uniformly in proportions, adding the bacterial enzyme synergistic fermentation feed prepared in step (3), and stirring the basic component and the bacterial enzyme synergistic fermentation feed uniformly.

* * * * *